(12) United States Patent
Chang et al.

(10) Patent No.: US 6,280,424 B1
(45) Date of Patent: Aug. 28, 2001

(54) APPARATUS AND METHOD FOR USING A NEEDLE IN AN INTRAVASCULAR ASSEMBLY

(75) Inventors: Joseph J. Chang, Irving; Donald D. Solomon, Southlake; Daniel M. Vincenzo, Hurst, all of TX (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/469,740

(22) Filed: Dec. 21, 1999

(51) Int. Cl.7 ...................................................... A61M 5/32
(52) U.S. Cl. .............................................................. 604/272
(58) Field of Search ..................................... 604/272, 274, 604/264, 164, 273, 170

(56) References Cited

U.S. PATENT DOCUMENTS

| | | | |
|---|---|---|---|
| 4,411,657 | * 10/1983 | Galindo | 604/274 |
| 4,784,638 | * 11/1988 | Ghajar et al. | 604/264 |
| 4,790,830 | * 12/1988 | Hamacher | 604/274 |
| 5,478,328 | * 12/1995 | Silverman et al. | 604/272 |
| 5,643,228 | * 7/1997 | Schucart et al. | 604/523 X |
| 5,848,996 | * 12/1998 | Eldor | 604/272 |

* cited by examiner

*Primary Examiner*—Manuel Mendez
(74) *Attorney, Agent, or Firm*—Blakely, Sokoloff, Taylor & Zafman

(57) ABSTRACT

An apparatus and method is disclosed in which an intravascular device allows blood to flow into a plurality of apertures longitudinally located in a portion of the needle.

11 Claims, 6 Drawing Sheets

APPARATUS AND METHOD FOR USING A NEEDLE IN AN INTRAVASCULAR ASSEMBLY

BACKGROUND OF THE INVENTION

1. Field of the Invention

The present invention relates generally to medical devices, and more particularly to a needle used in an intravascular assembly such as a catheter.

2. Description of Related Art

Intravascular assemblies such as catheter assemblies are generally used for passing fluids between a device such as a syringe or a drip to or from body lumens such as veins or arteries, or other internal target sites. A catheter assembly usually includes a hub, a catheter, and a needle. An eyelet ring is typically inserted into the catheter. The catheter, together with the eyelet ring, is then inserted into an opening in the nose of the hub and is secured to the hub by press fitting the eyelet ring within the nose of the hub. A needle is then inserted into the catheter. A sharp tip of the needle is used for piercing a body lumen so that access may be gained into the body lumen by the catheter and the needle. Once the catheter and the needle are located within the body lumen, the needle is removed. A syringe or a pipe of a drip is then attached to the hub so that fluids may be passed through the hub and the catheter between the drip or the syringe and the body lumen. The hub is typically made of materials that provide sufficient rigidity thereto and the catheter is usually made of a material which is flexible.

In the prior art, a notched needle is known such as that which is shown in FIG. 1. This needle has a large oval hole at the distal end of the needle for allowing early visualization of blood flashback. However, a large oval hole weakens the cannula's bending strength. Accordingly, there is a need for a needle that allows for early visualization of bodily fluids entering the cannula of the needle that avoids affecting the bending strength of the cannula.

SUMMARY OF THE INVENTION

An apparatus and method is disclosed in which an intravascular assembly having a needle allows blood to flow into a plurality of apertures longitudinally located in a portion of the needle. Additional features, embodiments, and benefits will be evident in view of the figures and detailed description presented herein.

BRIEF DESCRIPTION OF THE DRAWINGS

Features, aspects, and advantages of the invention will become more thoroughly apparent from the following detailed description, appended claims, and accompanying drawings in which:

DETAILED DESCRIPTION OF THE INVENTION

One embodiment of the invention relates to an intravascular assembly having a needle that includes a plurality of apertures that allow bodily fluids to flow into the needle thereby providing early visual feedback to a healthcare worker that a target site such as a vein has been located. A method of using such a needle is also disclosed.

The following detailed description and the accompanying drawings are provided for the purpose of describing and illustrating embodiments of the invention only, and are not intended to limit the scope of the invention in any way.

Figure 2:
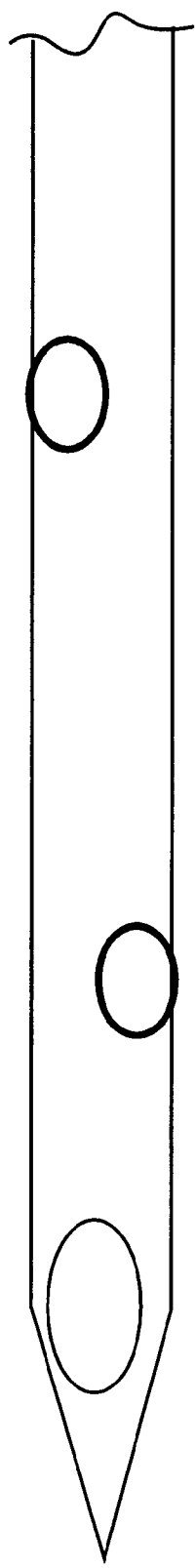
FIG. 2 is a cross-sectional view of a needle having a plurality of apertures longitudinally spaced in accordance with an embodiment of the invention.
Figure 3:
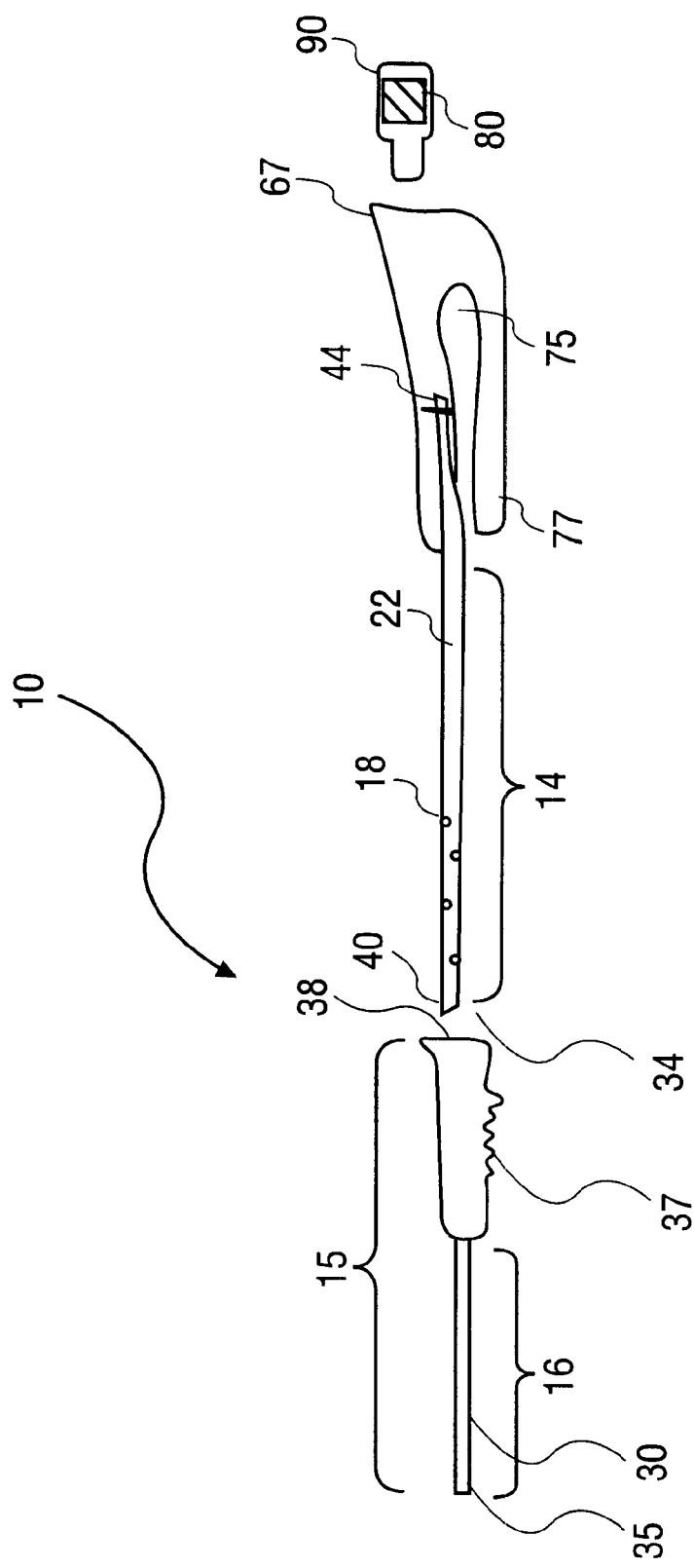
FIG. 3 shows an intravascular assembly in which a needle with a plurality of apertures are longitudinally spaced in accordance with an embodiment of the invention.

With reference to one embodiment of the invention shown in FIG. 2 there is provided assembly 10 that may be used to facilitate percutaneous insertion of an intravascular cannula, tube, and catheter. FIG. 2 shows assembly 10 generally comprises introducer 15, needle 18, and protective outer sheath 16.

Introducer 15 comprises an elongated tubular cannula 30 with a hollow lumen 35 extending longitudinally through cannula 30. A tapered distal tip is formed on the distal end of the cannula 30 to facilitate insertion and advancement of the cannula through skin, connective tissue, or a blood vessel wall.

Assembly 10 also includes housing 67 coupled to needle 18. At the proximal end of housing 67, member 90 is coupled thereto. Member 90 has a lower cylindrical portion that has an outside diameter that is smaller than the inner diameter of housing 67.

In the preferred embodiment, elongated needle 18 is formed of material such as stainless steel hypotubing and has a beveled or otherwise sharpened distal tip 40. As shown in FIG. 2, a hollow bore 22 extends longitudinally through needle 18. The apertures have a radius approximately in the range of 0.005" to 0.060". The distance between each aperture is approximately in the range of 0.025" to 0.300". In one embodiment of the invention, the apertures are radially biased. This radial bias may have a variety of ranges depending, in part, upon the thickness of the wall of needle 18. Preferably, the radial bias may range from 30 degrees to 50 degrees. The wall thickness of needle 18 may vary from approximately 0.004" to 0.010".

Figure 1:
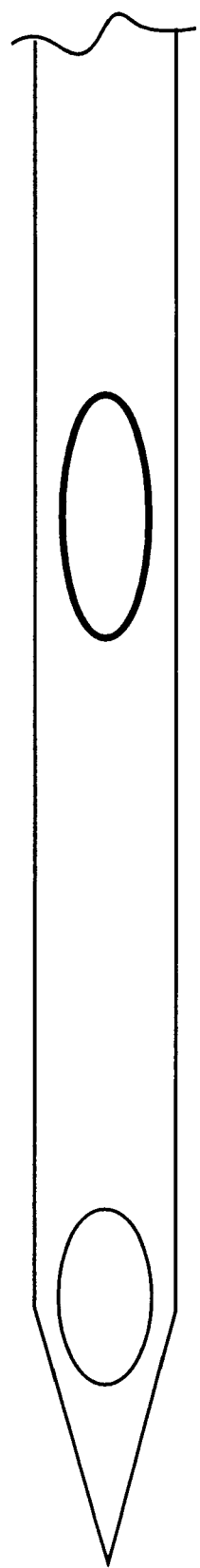
FIG. 1 is cross-sectional view of a needle of the prior art in which the needle has a hole longitudinally placed.

A transparent flash chamber housing 37 is coupled to the proximal end of the elongated rigid needle 18. A hollow flash chamber bore 38 extends longitudinally through the proximal flash chamber housing 37. Such longitudinal flash chamber bore 38 has a substantially cylindrical proximal inner wall of substantially continuous diameter and a narrowed or tapered distal inner wall 60. The hollow inner bore 38 of flash chamber housing 37 is continuous with and connected to the hollow bore 22 of needle 18 as shown in FIG. 1 wherein these elements are coaxially nestled together.

Figure 4:
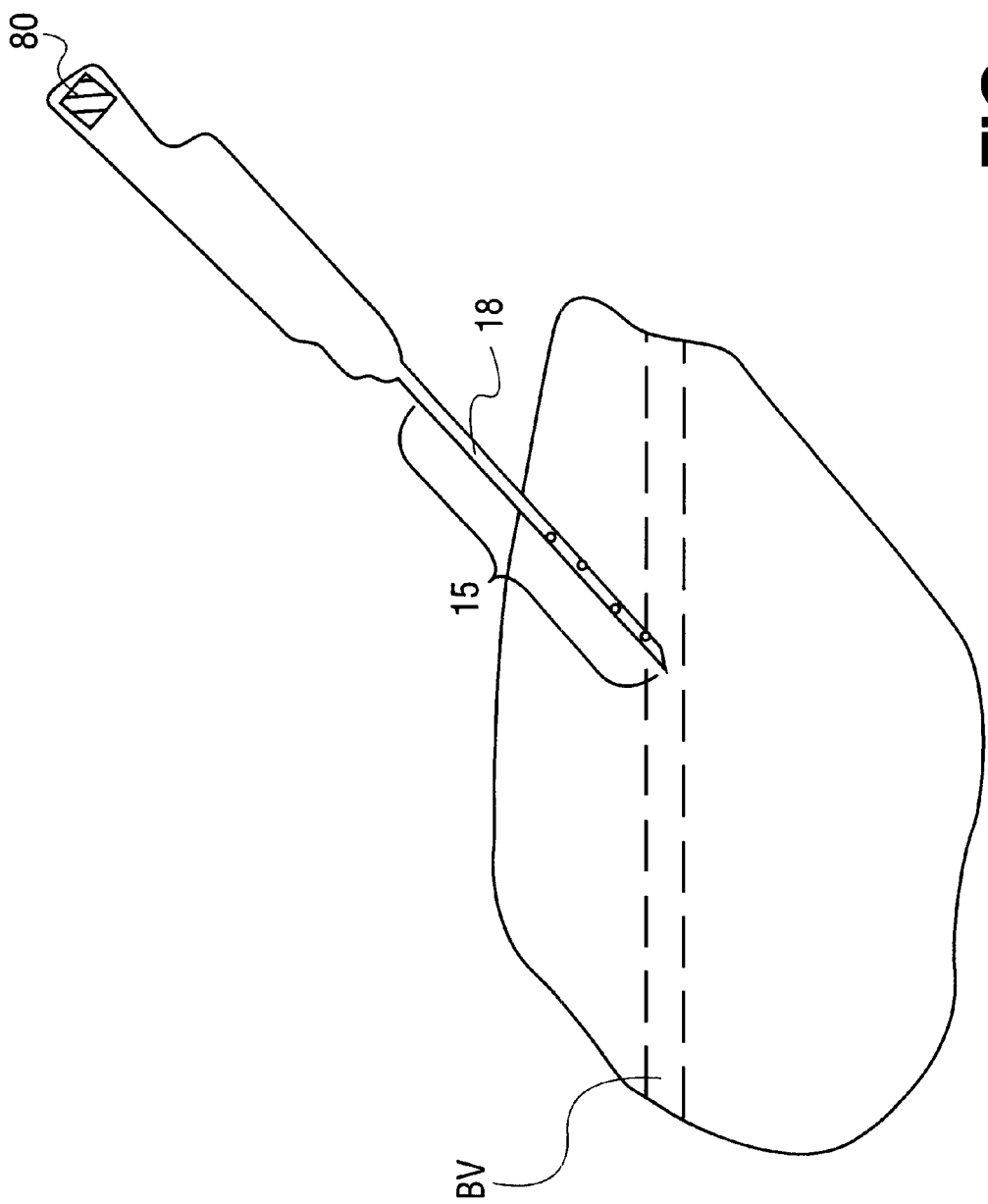
FIGS. 4 through 6 are a step-wise illustration of one method of using the assembly described herein.
Figure 5:
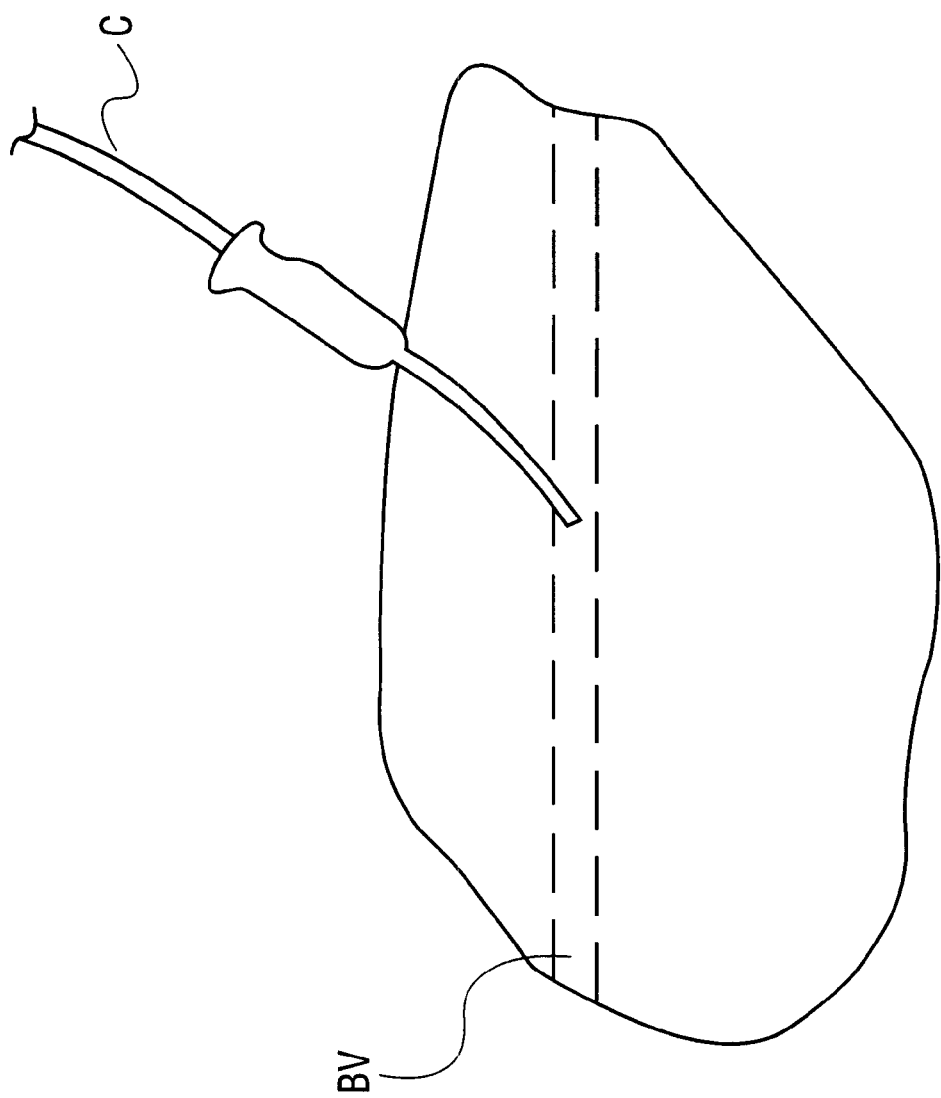
Figure 6:
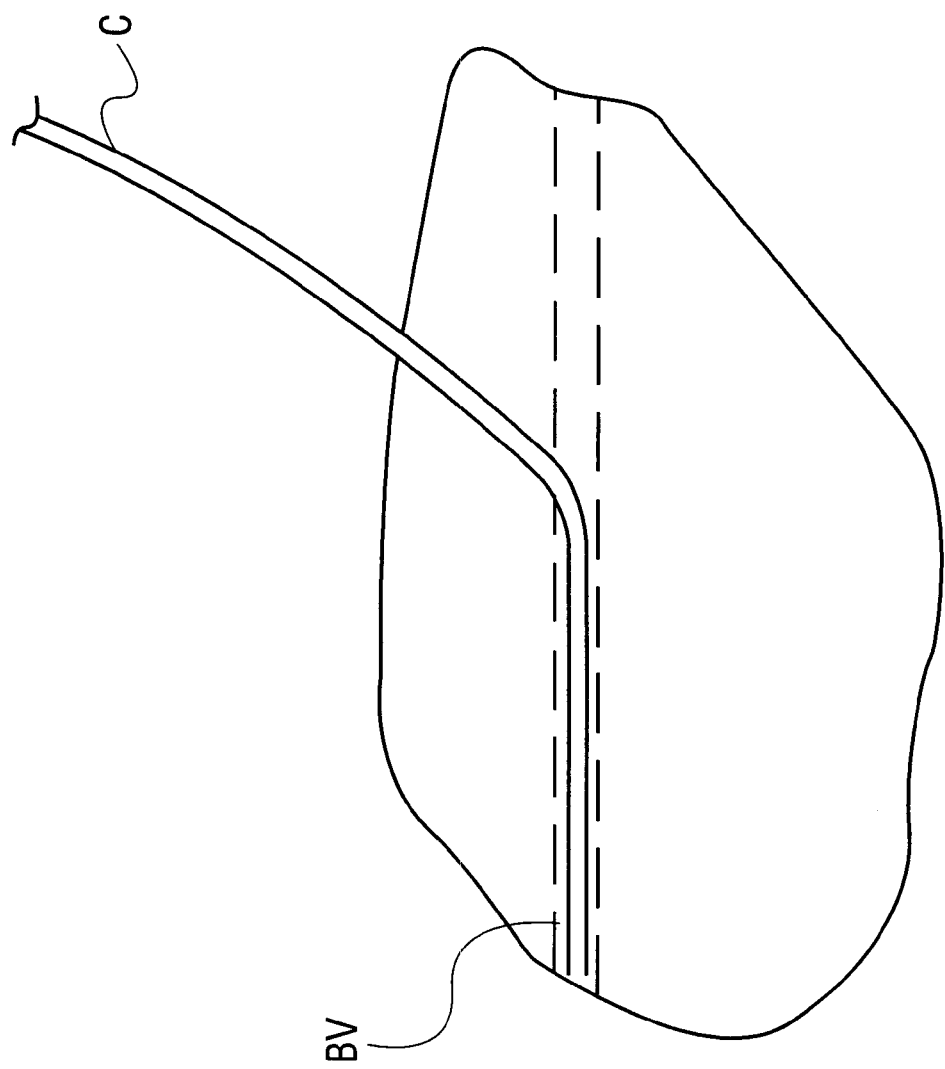

Given the above description, the flow of bodily fluids through assembly 10 may occur generally in the following fashion as shown in FIGS. 4 through 6. Needle 18 pierces the skin of a patient and enters a vessel such as a blood vessel. Blood or other bodily fluids enters the apertures located longitudinally in needle 18. Thereafter, the blood flows into the hollow cavity of needle 18 and moves generally in the direction of the proximal end of needle 18. The bodily fluid then enters flash chamber 37. Flash chamber 37 generally serves the purpose of containing bodily fluids. As flash chamber 37 fills with bodily fluid, the bodily fluid may contact barrier member 80. Barrier member 80, securely fitted into member 90 which is fastened to housing 67, prevents blood from exiting an intravascular assembly 10 and contacting a healthcare worker.

It will be appreciated that intravascular assembly 10 may be formed or configured in various different ways, without departing from its intended functions, including the function of supporting needle 18 having a plurality of apertures or holes located longitudinally in needle 18 which allows early visualization of that a target site such as a vein has been located by the distal tip of needle 18.

FIGS. 4 though 6 show one embodiment of the invention in which a catheter is inserted into a patient. Needle 18 having introducer 15 disposed thereon is percutaneously inserted into a blood vessel BV as shown in FIG. 4. The presence of blood in at least one of the plurality of apertures located longitudinally on needle 18 provides an indication to a healthcare worker that blood vessel BV has been entered.

After needle 18 has been removed and discarded, a tubular catheter C is advanced through the introducer 15, as shown in FIG. 5. FIG. 6 shows the introducer 15 is proximally withdrawn, leaving the catheter C within the blood vessel BV.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A catheter unit comprising:

a housing;

a needle coupled to the housing, the needle having a plurality of apertures located longitudinally along a cannula of the needle; and wherein the apertures are radially biased in an approximate range of 30 to 50 degrees.

2. The catheter unit of claim 1, wherein at least one of the apertures is substantially circular in shape.

3. The catheter unit of claim 1, wherein at least one aperture is approximately in the range of 0.025 to 0.300 inches distance from another aperture.

4. The catheter unit of claim 1, wherein a first aperture is approximately 0.25 inches from a second aperture.

5. The catheter unit of claim 1, wherein the apertures are substantially evenly spaced longitudinally.

6. The catheter unit of claim 1, wherein a radius of the aperture ranges from 0.005" to 0.060".

7. A catheter comprising:

a housing; and a needle coupled to the housing, the needle having a plurality of holes longitudinally placed in a cannula of the needle;

wherein the plurality of holes are radially biased in a range of about 30 to 50 degrees.

8. The catheter of claim 7 wherein a first hole is radially biased from a second hole approximately in the range of 30 to 50 degrees.

9. The catheter of claim 7 wherein the holes are substantially evenly spaced longitudinally.

10. A catheter device comprising:

a housing which transitions into a tube;

a needle secured to the housing, the needle having a plurality of apertures located longitudinally along a cannula of the needle; and the apertures are radially biased about 30 to 50 degrees.

11. The catheter device of claim 10, wherein the apertures are radially biased from 30 to 50 degrees.

\* \* \* \* \*